United States Patent
Rinaldi (10) Patent No.: US 7,735,490 B2
(45) Date of Patent: Jun. 15, 2010

(54) ADJUSTABLE NASAL CANNULA APPARATUS AND METHOD OF USE

(76) Inventor: Tracey Lyn Rinaldi, 14300 Morningside Dr., Atascadero, CA (US) 93422

( * ) Notice: Subject to any disclaimer, the term of this patent is extended or adjusted under 35 U.S.C. 154(b) by 1066 days.

(21) Appl. No.: 11/057,731

(22) Filed: Feb. 12, 2005

(65) Prior Publication Data

US 2006/0180151 A1    Aug. 17, 2006

(51) Int. Cl.
*A61M 16/08* (2006.01)
*A62B 9/04* (2006.01)

(52) U.S. Cl. .................. 128/207.18; 128/202.27; 128/204.18; 128/206.21; 128/912

(58) Field of Classification Search ........... 128/200.24, 128/203.22, 204.11, 204.12, 206.11, 207.13, 128/206.28, DIG. 26, 912, 207.15, 207.17, 128/202.27, 207.18, 201.22, 204.18, 206.21, 128/207.77

See application file for complete search history.

(56) References Cited

U.S. PATENT DOCUMENTS

| | | | | |
|---|---|---|---|---|
| 2,590,006 | A | | 3/1952 | Gordon ...................... 128/206 |
| 2,931,358 | A | | 4/1960 | Sheridan .................... 128/206 |
| 3,112,745 | A | * | 12/1963 | Boyer ..................... 128/201.23 |
| 3,802,431 | A | * | 4/1974 | Farr ....................... 128/207.18 |
| 4,106,505 | A | * | 8/1978 | Salter et al. ............. 128/207.18 |
| 4,278,082 | A | * | 7/1981 | Blackmer ............... 128/207.18 |
| 4,406,283 | A | | 9/1983 | Bir ............................. 128/207 |
| 4,422,456 | A | * | 12/1983 | Tiep ....................... 128/207.18 |
| 4,593,690 | A | * | 6/1986 | Sheridan et al. ........ 128/207.15 |
| 4,622,965 | A | * | 11/1986 | Teeple .................... 128/207.14 |
| 4,774,946 | A | * | 10/1988 | Ackerman et al. ..... 128/207.18 |
| 4,808,160 | A | * | 2/1989 | Timmons et al. ......... 604/94.01 |
| 4,852,564 | A | * | 8/1989 | Sheridan et al. ........ 128/202.27 |
| 4,878,491 | A | * | 11/1989 | McGilvray, III ........ 128/201.11 |
| 5,024,220 | A | * | 6/1991 | Holmgreen et al. ..... 128/207.18 |
| 5,106,505 | A | * | 4/1992 | Taylor ........................ 210/640 |
| 5,137,017 | A | | 8/1992 | Salter ..................... 128/207.18 |
| 5,400,776 | A | * | 3/1995 | Bartholomew ......... 128/200.24 |
| 5,477,852 | A | * | 12/1995 | Landis et al. ........... 128/207.18 |
| 5,636,630 | A | | 6/1997 | Miller et al. ............ 128/207.17 |
| 5,645,058 | A | | 7/1997 | Odom .................... 128/207.18 |
| 5,682,881 | A | * | 11/1997 | Winthrop et al. ....... 128/207.18 |
| 5,687,715 | A | | 11/1997 | Landis et al. ........... 128/207.18 |
| 5,704,916 | A | | 1/1998 | Byrd ........................... 604/179 |
| 5,769,702 | A | * | 6/1998 | Hanson ........................ 454/63 |
| 5,797,392 | A | * | 8/1998 | Keldmann et al. ...... 128/203.15 |
| 6,247,470 | B1 | | 6/2001 | Ketchedjian ............ 128/200.28 |
| 6,298,850 | B1 | | 10/2001 | Argraves ................ 128/207.17 |
| 6,398,266 | B1 | * | 6/2002 | Crump ........................ 285/226 |
| 6,440,120 | B1 | * | 8/2002 | Maahs .......................... 604/523 |
| 6,533,983 | B2 | * | 3/2003 | Curti ........................... 264/219 |
| 6,561,193 | B1 | * | 5/2003 | Noble .................... 128/207.18 |
| 6,684,883 | B1 | | 2/2004 | Burns .................... 128/207.18 |
| 6,772,761 | B1 | * | 8/2004 | Rucker, Jr. ............. 128/207.14 |
| 6,889,689 | B1 | * | 5/2005 | Neuman ................ 128/201.22 |
| 7,004,170 | B1 | * | 2/2006 | Gillstrom ............... 128/207.18 |
| 7,156,097 | B2 | * | 1/2007 | Cardoso ................ 128/206.11 |

(Continued)

*Primary Examiner*—Justine R Yu
*Assistant Examiner*—Clinton Ostrup
(74) *Attorney, Agent, or Firm*—Philip A Steiner (57) ABSTRACT

A nasal cannula apparatus which includes one or more adjustment members which allow a wearer of the apparatus to retentively reposition the fluid supply tubing to a desired position of comfort. The ability to retentively reposition minimizes the dermal abrasion problems of the ears and other portions of the face experienced by the prolonged wearing of the nasal cannula apparatus encountered in the current art.

4 Claims, 6 Drawing Sheets

U.S. PATENT DOCUMENTS

| | | | |
|---|---|---|---|
| 7,178,528 B2 * | 2/2007 | Lau et al. | 128/207.18 |
| 2005/0028821 A1 * | 2/2005 | Wood et al. | 128/207.18 |
| 2005/0092329 A1 * | 5/2005 | Sta-Maria | 128/207.18 |
| 2005/0103331 A1 * | 5/2005 | Wedemeyer | 128/200.24 |
| 2006/0278232 A1 * | 12/2006 | Nichols | 128/206.11 |

* cited by examiner

ADJUSTABLE NASAL CANNULA APPARATUS AND METHOD OF USE

CROSS-REFERENCE TO RELATED APPLICATIONS

Not Applicable

FEDERALLY SPONSORED RESEARCH AND DEVELOPMENT

Not Applicable

REFERENCE TO A MICROFICHE APPENDIX

Not Applicable

FIELD OF INVENTION

The present invention relates generally to a medical insufflating apparatus, and more specifically to a nasal cannula apparatus having one or more adjustable members which allows a wearer to manually position and maintain fluid supply tubing away from substantially contacting the ears of the wearer.

BACKGROUND

Nasal cannula apparatus provides the wearer with supplemental fluids, typically, but not exclusively, oxygen, to help compensate for reduced pulmonary function arising from such diseases as emphysema, severe bronchitis and other cardiopulmonary maladies caused by disease progression or trauma. In the relevant art, the nasal cannula are typically held in place by having one or more fluid supply tubes rest upon the upper surfaces of the ears and sides of the head adjacent to the ears as a means of support.

In many cases, the nasal cannula must be worn for prolonged periods of time which results in significant irritation, ulceration and possible microbial infection of the skin at the points of contact with the ears and sides of the head. Moreover, many of these unfortunate individuals require the supplemental fluids to be provided at all times for their very survival. As such, the wounds induced by the fluid supply tubes have little chance to heal.

An example of a very common nasal cannula arrangement is disclosed in U.S. Pat. No. 4,106,505 to Salter, et al., which is hereby incorporated by reference in its entirety. The invention to Salter attempts to solve a significant contact irritation problem which occurs at the nostrils and upper lip of the wearer.

While the nostril area is more prone to irritation due to moisture, greater concentrations of invasive bacteria and friction transferred to the cannula by the wearer's head movements, this common arrangement transfers the contact irritation problem from the nostril area to portions of the ears and sides of the wearer's head and is therefore not a complete solution for those individuals requiring constant fluid supplementation or otherwise have skin sensitized to the plastics used to form the fluid supply tubes. Therefore, there is a need for a nasal cannula apparatus which is repositionable by the wearer to a more comfortable position about the head of the wearer.

SUMMARY

The invention addresses the limitations described above and provides a nasal cannula apparatus which allows the wearer to retentively position the fluid supply tubes away from the ears.

In a first aspect of the invention, a nasal cannula apparatus is disclosed comprising at least one fluid supply tube having contiguously coupled thereto; a nasal insufflating member and at least one adjustment member configured to maintain the contiguous flow path between the fluid supply tube and the nasal insufflating member. In this first aspect of the invention, the adjustment member includes memory means for maintaining a position set by the wearer of the nasal cannula apparatus, such that the fluid supply tube may be positioned to avoid substantial contact with an ear of the wearer.

In one embodiment of this first aspect of the invention, the adjustment member comprises a bellows joint member having a first nozzle and a second nozzle mounted in opposition along a long axis of the bellows joint member and coaxial with the at least one fluid supply tube first and the second nozzles are dimensioned to sealingly fit within or over a portion of the fluid supply tube.

In another embodiment of this first aspect of the invention, the adjustment member is constructed from a polymeric material, a malleable non-magnetic metallic material or a combination of the polymeric and a malleable non-magnetic metallic material.

In another embodiment of this first aspect of the invention, the adjustment member is coaxially coupled to the fluid supply tube at a position in proximity to the nasal insufflating member.

In yet another embodiment of this first aspect of the invention the adjustment member consists essentially of a generally tubular member having a first nozzle and a second nozzle mounted in opposition along a long axis of the tubular insert and coaxial with the fluid supply tube. In a related embodiment of this first aspect of the invention, the adjustment member comprises a malleable non-ferromagnetic metal joint constructed from one of aluminum, copper or austenitic stainless steel.

In a final embodiment of this first aspect of the invention, the adjustment member consists essentially of a malleable non-ferromagnetic metal member embedded longitudinally along at least a portion of the fluid supply tube. In a related embodiment of this first aspect of the invention, the adjustment member comprises a malleable non-ferromagnetic metal joint constructed from one of aluminum, copper or austenitic stainless steel.

In a second aspect of the invention, a nasal cannula apparatus is disclosed comprising a first fluid supply tube and a second fluid supply tube, where the first and the second fluid supply tubes are arranged generally in parallel and separable from each other. The first fluid supply tube includes a first end coupled to a first part of a Y-fitting. A second end of the first fluid supply tubing is coupled to a first part of a first adjustment means. A first supply segment tube having a first segment end is coupled to a second part of the first adjustment means and a second segment end is coupled to a first part of a second adjustment means.

A second supply segment tube having a first segment end is coupled to a second part of the second adjustment means, and a second segment end is coupled to a first part of a nasal insufflating member.

The second fluid supply tube includes a first end coupled to a second part of the Y-fitting; a second end coupled to a first part of a third adjustment means; and, a third supply segment tube having a first segment end coupled to a second part of the third adjustment means; a second segment end coupled to a first part of a fourth adjustment means; and, a fourth supply segment tube having a first segment end coupled to a second part of the third adjustment means; a second segment end coupled to a second part of the nasal insufflating member; a common fluid inlet supply tube coupled to a third part of the Y-fitting such that the first supply tube and the second supply tube form a closed fluid supply loop which discharges into the first and the second parts of the nasal insufflating member; and, a retaining means for maintaining the first fluid supply tube and the second fluid supply tube in proximity to the Y-fitting.

In one embodiment of this second aspect of the invention, at least one of the first, second, third and fourth adjustment means includes memory means for maintaining a position set by a wearer of the nasal cannula apparatus, such that at least one of the first or the second fluid supply tubes may be positioned to avoid substantial contact with an ear of a wearer.

In another embodiment of this second aspect of the invention, the first and the second adjustment means and at least one of the third and the fourth adjustment means includes memory means for maintaining at least one position set by a wearer of the nasal cannula apparatus, such that both the first and the second fluid supply tubes may be individually positioned to avoid substantial contact with one or more ears of a wearer.

In a final embodiment of this second aspect of the invention, the first and the second adjustment means and at least one of the third and the fourth adjustment means includes a bellows joint member, each bellows joint member having a first nozzle and a second nozzle mounted in opposition along a long axis of each of the bellows joint members.

In a third aspect of the invention, a nasal cannula apparatus is disclosed comprising a first fluid supply tube and a second fluid supply tube, where the first and the second fluid supply tubes being arranged generally in parallel and separable from one another; the first fluid supply tube having a first end coupled to a first part of a Y-fitting; a second end coupled to a first part of a nasal insufflating member; and the second fluid supply tube having; a first end coupled to a second part of the Y-fitting; a second end coupled to a second part of the nasal insufflating member; and, the adjustment means for maintaining a position set by a wearer of the nasal cannula apparatus, such that at least one of the first or the second fluid supply tubes may be positioned to avoid substantial contact with an ear of a wearer.

In one embodiment of this third aspect of the invention, the adjustment means includes one of a non-ferromagnetic metal ribbon and a non-ferromagnetic metal wire embedded in at least a portion of one of the first fluid supply tube or the second fluid supply tube.

In a related embodiment of this third aspect of the invention the non-ferromagnetic metal ribbon is embedded along at least a portion of a long axis of at least one of the first fluid supply tube and the second fluid supply tube.

In a second embodiment of this third aspect of the invention, the adjustment means comprises a polymeric sleeve coaxially mounted externally along a long axis of at least a portion and at least one of the first fluid supply tube and the second fluid supply tube, where the polymeric sleeve has embedded either a non-ferromagnetic ribbon or a non-ferromagnetic wire.

In a first methodic aspect for using the nasal cannula apparatus described above comprises positioning the nasal insufflating member in proximity to at least one nostril of the wearer; and manually adjusting the at least one adjustment member such that the at least one fluid supply tube avoids substantial contact with the ear of the wearer.

In a second methodic aspect for using the nasal cannula apparatus described above comprises positioning the nasal insufflating member in proximity to at least one nostril of a wearer; positioning the first fluid supply tube around one side of a head of the wearer; positioning the second fluid supply tube around the other side of the head of the wearer; and, manually adjusting the at least one of the first adjustment means, the second adjustment means, the third adjustment means and the fourth adjustment means such that the at least one of the first fluid supply tube and the second fluid avoids substantial contact with an ear of the wearer.

In a third methodic aspect for using the nasal cannula apparatus described above comprises positioning the nasal insufflating member in proximity to at least one nostril of the wearer; positioning the first fluid supply tube around one side of a head of the wearer; positioning the second fluid supply tube around the other side of the head of the wearer; and manually adjusting the at least one of the adjustment means, such that the at least one of the first fluid supply tube and the second fluid avoids substantial contact with the ear of the wearer.

BRIEF DESCRIPTION OF DRAWINGS

The features and advantages of the invention will become apparent from the following detailed description when considered in conjunction with the accompanying drawings. Where possible, the same reference numerals and characters are used to denote like features, elements, components or portions of the invention. Optional components are generally shown in dashed lines. It is intended that changes and modifications can be made to the described embodiment without departing from the true scope and spirit of the subject invention as defined in the claims.

DETAILED DESCRIPTION

This present invention provides a wearer of nasal cannula apparatus the ability to reposition the fluid supply tubes to be oriented in a more comfortable position by adding lightweight flexible polymeric joints and/or malleable non-ferromagnetic metals to the nasal cannula apparatus as is described in the various aspects and embodiments of the inventions provided below.

Figure 1:
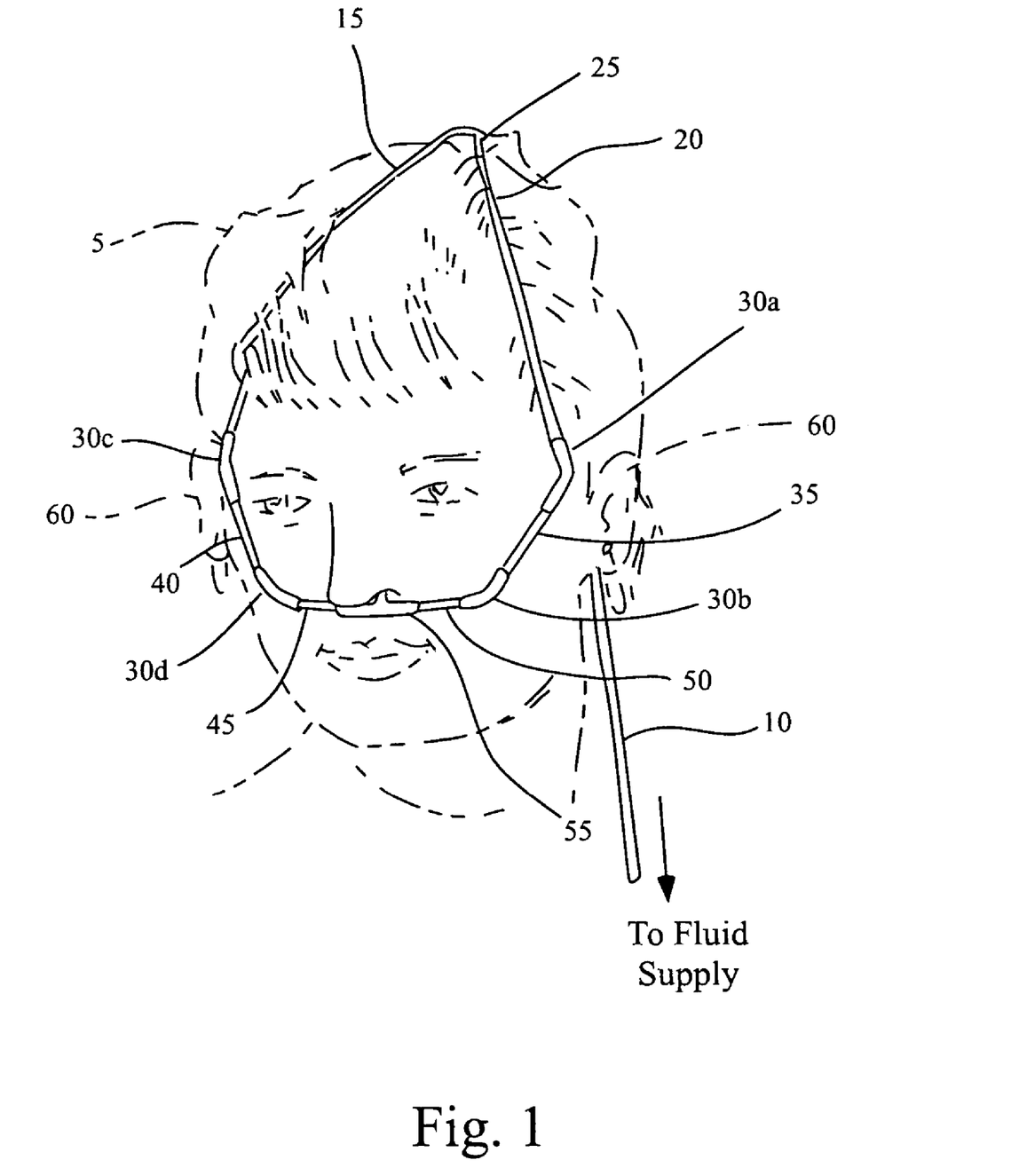
FIG. 1—is a frontal view of an aspect of the invention in which a wearer has retentively positioned fluid supply tubes away from his or her ears.

Referring to FIG. 1, a first exemplary embodiment of the invention is shown in which a wearer 5 has comfortably positioned a nasal cannula apparatus away from the ears 60.

The nasal cannula apparatus includes a first fluid supply tube 20 which is joined to an inlet side of a first adjustment member 30a. A first fluid supply tube segment 35 is joined to the outlet side of the first adjustment member 30a at one end and is joined to an inlet side of a second adjustment member 30b at the opposite end. A second fluid supply tube segment 50 is joined to the outlet side of the second adjustment member 30 be at one end and to a first inlet side of a nasal insufflating member 55 at its opposite end.

Likewise, a second fluid supply tube 15 is joined to an inlet side of a third adjustment member 30c. A third fluid supply tube segment 40 is joined to the outlet side of the third adjustment member 30c at one end and to an inlet side of a fourth adjustment member 30d at the opposite end. A fourth fluid supply tube segment 45 is joined to the outlet side of the fourth adjustment member 30d at one end and to a second inlet side of the nasal insufflating member 55 at its opposite end.

Figure 1A:
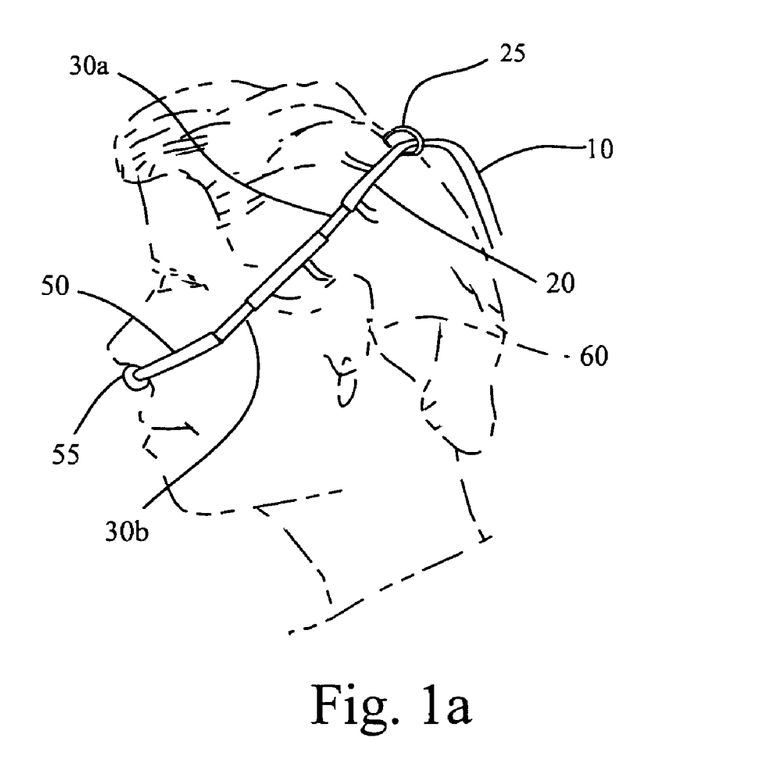
FIG. 1*a*—is a side view of an aspect of the invention in which a wearer has retentively positioned fluid supply tubes away from his or her ears.
Figure 1B:
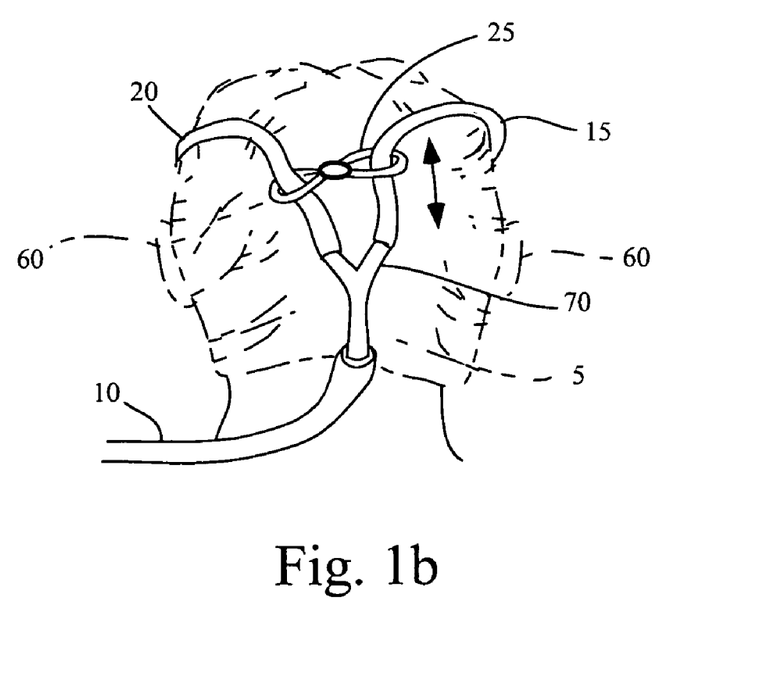
FIG. 1*b*—is a rear view of an aspect of the invention in which a wearer has retentively positioned fluid supply tubes away from his or her ears.

In this embodiment of the invention, the first and second fluid supply tubes 20, 15 are shown routed over the top the wearer's head 5 and held in position by a retaining clip 25 depicted in FIGS. 1a, 1b.

The diameters of the first and second fluid supply tubes 20, 15 and the first, second, third, and fourth supply tube segments 35, 40, 45, 50 are generally equal and constructed of like polymeric materials to ensure a balanced fluid flow is delivered to the nasal insufflating member 55.

A larger diameter common fluid supply tube 10 delivers the fluid from a reservoir to the first and second fluid supply tubes 20, 15 by way of a Y-fitting 70 depicted in FIG. 1b. The first, second, third and fourth adjustment members 30a, 30b, 30c, 30d are coaxially joined to the first and second fluid supply tubes 20, 15 and the first, second, third, and fourth supply tube segments 35, 40, 45, 50 so as to not interfere with the fluid supply being delivered to the wearer 5.

While four adjustment members 30a, 30b, 30c, 30d are shown in this figure, one skilled in the art will appreciate that fewer adjustment members could be used to allow the wearer to reposition the fluid supply tubes to achieve a more comfortable position.

The polymeric construction materials of the first and second fluid supply tubes 20, 15, the first, second, third, and fourth supply tube segments 35, 40, 45, 50 and common fluid supply tube 10 are preferably of a thermo plastic such as polyvinyl chloride (PVC) having a sufficient plasticizer to allow flexibility and suppleness. PVC or other common thermo plastic polymers used in the current art are acceptable for use in the various components incorporated into the invention. Additional construction materials may be incorporated or replace the polymeric construction of the first, second, third and fourth adjustment members 30a, 30b, 30c, 30d as described below.

Figure 2A:
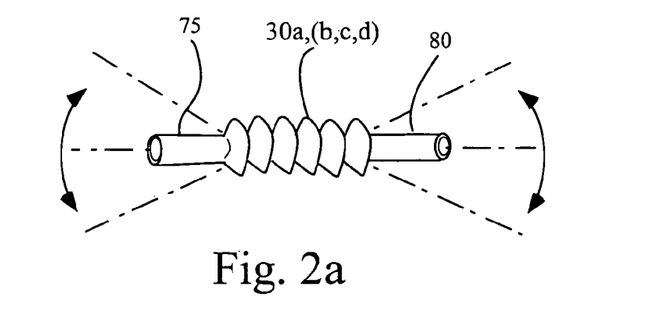
FIGS. 2*a*-2*d*—depicts an aspect of the invention that incorporates a flexible bellows joint as an adjustment member.

Referring to FIG. 2a, a first embodiment of the invention is depicted. In this embodiment of the invention, a flow through adjustable bellows joint (adjustment member) 30a is disposed into the nasal cannula invention at two or more of the adjustment member positions 30a, 30b, 30c, 30d depicted in FIG. 1.

The bellows joint(s) 30a are constructed with inlet 75 and outlet nozzles 80 for attachment to the first and second fluid supply tubes 20, 15, and/or the first, second, third, and fourth supply tube segments 35, 40, 45, 50. The designation of inlet and outlet are used for convenience only. The adjustment members are intended to be simple flow-through devices which lack flow directivity restrictions.

Figure 2B:
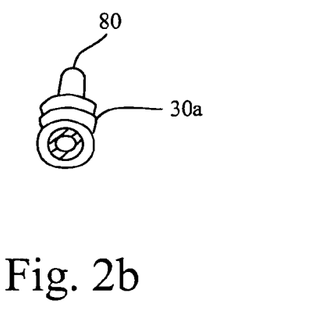

The adjustment members, as is depicted in FIG. 2b, are constructed of polymeric materials which are compatible with the polymeric construction materials of the first and second fluid supply-tubes 20, 15, and/or the first, second, third, and fourth supply tube segments 35, 40, 45, 50.

To achieve the necessary flexibility, positioning memory and structural integrity, a more rigid construction of polymer is used. For example, PVC having a reduced amount of plasticizer as is common used in the non-analogous art of drinking straws with flexible elbow joints.

Figure 2C:
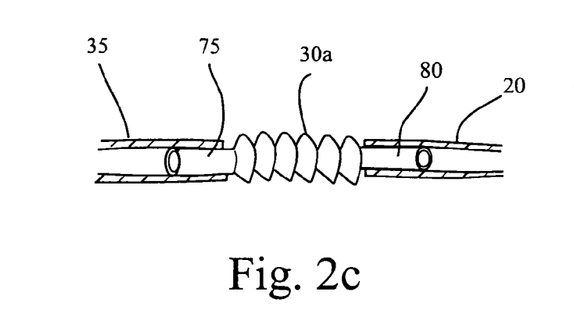

In one embodiment of the invention, depicted in FIG. 2c, the adjustment members 30a are dimensioned to fit into the first and second fluid supply tubes 20, 15, and/or the first, second, third, and fourth supply tube segments 35, 40, 45, 50. In this embodiment of the invention, the outer diameters of the inlet and outlet nozzles 75, 80 are slightly larger than the inner diameters of the fluid supply tubing 35, 20. The resilient properties of the dimensionally expanded fluid supply tubing 35, 20 forms sealed joints over the inlet and outlet nozzles 75, 80. This tubing coupling arrangement is commonly employed in the non-analogous art of aquarium aeration tubing. Alternately, the inlet and outlet nozzles may be attached to the various fluid supply tubing using an adhesive.

The various inner and outer diameters of the first and second fluid supply tubes 20, 15, the first, second, third, and fourth supply tube segments 35, 40, 45, 50 and/or the inlet and outlet nozzles 75, 80 may be adjusted accordingly to optimize the fluid flow delivered to the nasal insufflating member 55 depicted in FIG. 1.

Figure 2D:
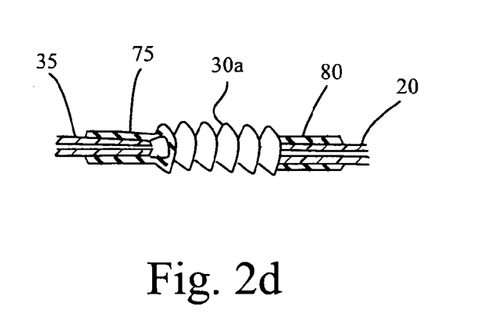

In another related embodiment of the invention, depicted in FIG. 2d, the adjustment members 30a are dimensioned to fit over the first and second fluid supply tubes 20, 15, and/or the first, second, third, and fourth supply tube segments 35, 40, 45, 50. In this embodiment of the invention, the inner diameters of the inlet and outlet nozzles 75, 80 are slightly smaller in diameter than the fluid supply tubing 35, 20. The resilient properties of the dimensionally compressed fluid supply tubing 35, 20 forms sealed joints within the inlet and outlet nozzles 75, 80. Alternately, the inlet and outlet nozzles 75, 80 may be attached to the various fluid supply tubing using an adhesive.

As before, the various diameters of the first and second fluid supply tubes 20, 15, the first, second, third, and fourth supply tube segments 35, 40, 45, 50 and/or the inlet and outlet nozzles 75, 80 may be varied accordingly to optimize the fluid flow delivered to the nasal insufflating member 55 depicted in FIG. 1.

Both embodiments of the invention depicted in FIGS. 2c and 2d may be used to retrofit an existing nasal cannula available in the current art or provided as a complete nasal cannula assembly. Inclusion of the bellows joints as adjustment members 30a, 30b, 30c, 30d allows a wearer 5 of the nasal cannula to adjust various portions of the fluid supply tubing to achieve a more comfortable wearing position. Wearing adjustment is made simply by repositioning of the applicable section(s) of the supply tubing and flexing of the bellows joints (adjustment members 30a, 30b, 30c, 30d) depicted in FIG. 1.

Figure 3A:
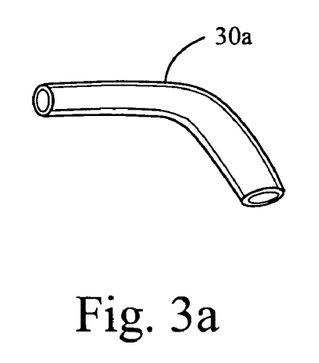
FIG. 3*a*-3*d* depicts an aspect of the invention that incorporates a non-ferromagnetic metal tube as an adjustment member.

Referring to FIG. 3a, another embodiment of the invention is depicted. In this embodiment of the invention, a flow through adjustable joint 30a is disposed into the nasal cannula invention at two or more of the adjustment member positions 30a, 30b, 30c, 30d depicted in FIG. 1. The flow through adjustment member 30a is uniform in diameter for direct attachment to the first and second fluid supply tubes 20, 15, and/or the first, second, third, and fourth supply tube segments 35, 40, 45, 50.

Figure 3B:
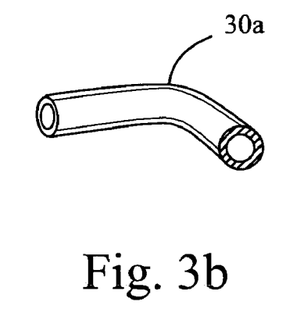

The adjustment member 30a, as is depicted in FIG. 3b, is constructed of one or more non-ferromagnetic metals that are compatible with the polymeric construction materials of the first and second fluid supply tubes 20, 15, and/or the first, second, third, and fourth supply tube segments 35, 40, 45, 50. For example, non-ferromagnetic metal tubing constructed from aluminum, copper or austenitic stainless steel may be used for the adjustment members 30a. Non-ferromagnetic metals are important for wearers who may undergo magnetic resonance imaging (MRI) procedures. If MRI procedures are not of concern, iron alloys may be employed as well.

To achieve the necessary flexibility, positioning memory and structural integrity, the wall thicknesses of the metal tubing comprising the adjustment member 30a is optimized to allow the tubing to bend without reaching the ductility limit(s) of the metal.

Figure 3C:
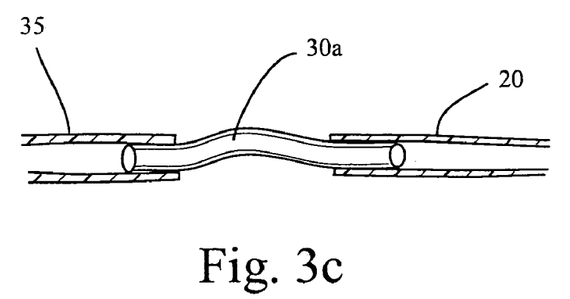

In one embodiment of the invention, depicted in FIG. 3c, the adjustment member 30a is dimensioned to fit into the first and second fluid supply tubes 20, 15, and/or the first, second, third, and fourth supply tube segments 35, 40, 45, 50. In this embodiment of the invention, the outer diameter of the metal adjustment member 30a is dimensioned slightly larger than the inner diameters of the fluid supply tubing 35, 20. The resilient properties of the dimensionally expanded fluid supply tubing 35, 20 forms sealed joints over the adjustment member 30a. Alternately, the adjustment member 30a may be attached to the various fluid supply tubing using an adhesive.

The various inner and outer diameters of the first and second fluid supply tubes 20, 15, the first, second, third, and fourth supply tube segments 35, 40, 45, 50 and/or the inlet and outlet nozzles 75, 80 may be varied accordingly to optimize the fluid flow delivered to the nasal insufflating member 55 depicted in FIG. 1.

Figure 3D:
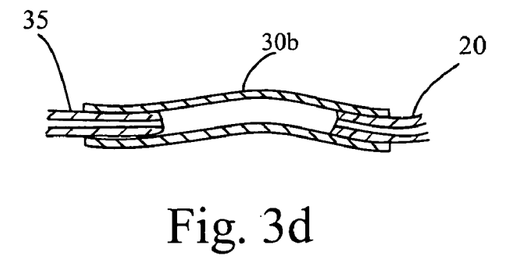

In another related embodiment of the invention, depicted in FIG. 3d, the adjustment member 30a is dimensioned to fit over the first and second fluid supply tubes 20, 15, and/or the first, second, third, and fourth supply tube segments 35, 40, 45, 50. In this embodiment of the invention, the inner diameter of the adjustment member 30a is slightly smaller in diameter than the fluid supply tubing 35, 20. The resilient properties of the dimensionally compressed fluid supply tubing 35, 20 forms sealed joints within the adjustment member 30a. Alternately, the adjustment member 30a may be attached to the various fluid supply tubing using an adhesive.

As previously described, the various diameters of the first and second fluid supply tubes 20, 15, the first, second, third, and fourth supply tube segments 35, 40, 45, 50 and/or the inlet and outlet nozzles 75, 80 may be varied accordingly to optimize the fluid flow delivered to the nasal insufflating member 55 depicted in FIG. 1.

Both embodiments of the invention depicted in FIGS. 3c and 3d may be used to retrofit an existing nasal cannula available in the current art or provided as a complete nasal cannula assembly. Inclusion of the metal adjustment members 30a, 30b, 30c, 30d allows a wearer 5 of the nasal cannula to adjust various portions of the fluid supply tubing to achieve a more comfortable wearing position. Wearing adjustment is made simply by bending of the applicable section(s) of the of the adjustment members 30a, 30b, 30c, 30d depicted in FIG. 1.

Figure 4A:
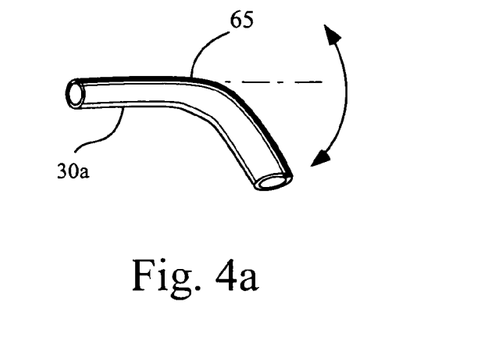
FIGS. 4*a*-4*e* depicts an aspect of the invention that incorporates a polymeric joint having a non-ferromagnetic ribbon or wire embedded therein as an adjustment member

Referring to FIG. 4a, another embodiment of the invention is depicted. In this embodiment of the invention a flow through flexible polymeric joint (adjustment member) 30a is disposed into the nasal cannula invention at two or more of the adjustment member positions 30a, 30b, 30c, 30d depicted in FIG. 1.

Figure 4B:
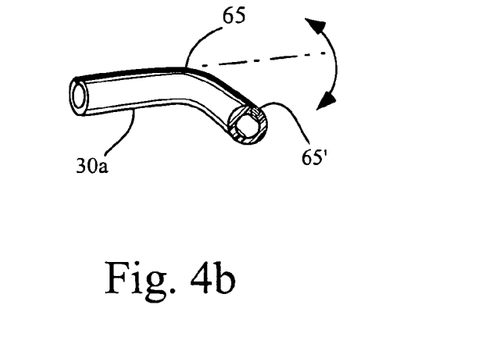

The polymeric joint 30a as depicted in FIG. 4b, is constructed primarily of polymeric materials which is compatible with the polymeric construction materials of the first and second fluid supply tubes 20, 15, and/or the first, second, third, and fourth supply tube segments 35, 40, 45, 50. In addition, a thin non-ferromagnetic metal ribbon or wire 65, 65' is incorporated along a long axis of the polymeric joint (adjustment member) 30a. The addition of the thin non-ferromagnetic metal ribbon or wire 65, 65' provides the necessary positioning memory not generally available in the inexpensive thermoplastic polymers normally found in nasal cannula constructions.

The metal ribbon or wire 65, 65' may extruded with the thermoplastic tubing at the time of tubing manufacture or added thereafter by heating the ribbon or wire 65, 65' beyond the melting point of the thermoplastic and embedding the metal into polymeric tubing.

In both of the aforementioned manufacturing methods, the metal ribbon or wire 65, 65' should be embedded entirely in the polymeric construction of the tubing rather than extending into the fluid flow channel. This reduces the chances of oxidation and possible reaction if high concentrations of oxygen are to be used as the fluid provided to the wearer.

Figure 4C:
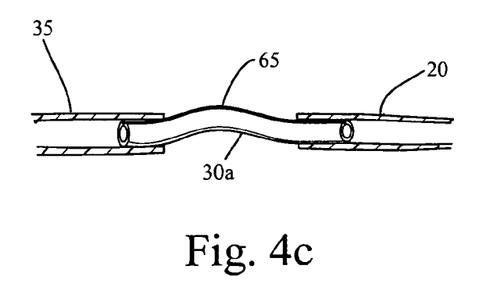

In one embodiment of the invention, depicted in FIG. 4c, the adjustment member 30a is dimensioned to fit into the first and second fluid supply tubes 20, 15, and/or the first, second, third, and fourth supply tube segments 35, 40, 45, 50. In this embodiment of the invention, the outer diameter of the adjustment member 30a is dimensioned slightly larger than the inner diameters of the fluid supply tubing 35, 20. The resilient properties of the dimensionally expanded fluid supply tubing 35, 20 forms sealed joints over the adjustment member 30a. Alternately, the adjustment member 30a may be attached to the various fluid supply tubing using an adhesive.

The various inner and outer diameters of the first and second fluid supply tubes 20, 15, the first, second, third, and fourth supply tube segments 35, 40, 45, 50 and/or the inlet and outlet nozzles 75, 80 may be varied accordingly to optimize the fluid flow delivered to the nasal insufflating member 55 depicted in FIG. 1.

Figure 4D:
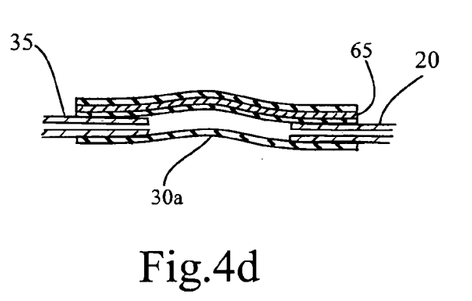

In another related embodiment of the invention, depicted in FIG. 4d, the adjustment member 30a is dimensioned to fit over the first and second fluid supply tubes 20, 15, and/or the first, second, third, and fourth supply tube segments 35, 40, 45, 50. In this embodiment of the invention, the inner diameter of the adjustment member 30a is slightly smaller in diameter than the fluid supply tubing 35, 20. The resilient properties of the dimensionally compressed fluid supply tubing 35, 20 forms sealed joints within the adjustment member 30a. Alternately, the adjustment member 30a may be attached to the various fluid supply tubing using an adhesive.

As previously described, the various diameters of the first and second fluid supply tubes 20, 15, the first, second, third, and fourth supply tube segments 35, 40, 45, 50 and/or the inlet and outlet nozzles 75, 80 may be varied accordingly to optimize the fluid flow delivered to the nasal insufflating member 55 depicted in FIG. 1.

Both embodiments of the invention depicted in FIGS. 4c and 4d may be used to retrofit an existing nasal cannula available in the current art or provided as a complete nasal cannula assembly. Inclusion of the adjustment members 30a, 30b, 30c, 30d allows a wearer 5 of the nasal cannula to adjust various portions of the fluid supply tubing to achieve a more comfortable wearing position. Wearing adjustment is made simply by bending of the applicable section(s) of the of the adjustment members 30a, 30b, 30c, 30d depicted in FIG. 1.

Figure 4E:
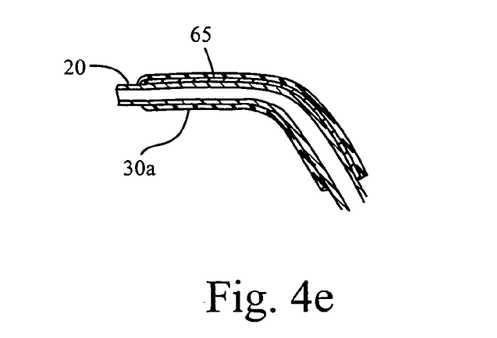

Referring to FIG. 4e, another embodiment of the invention is depicted where the adjustment member 30a is dimensioned to slidably fit over the first and second fluid supply tubes 20, 15, becoming a slidable sleeve which may be repositioned anywhere along the contiguous outer surfaces of the first and second fluid supply tubes 20, 15. As such, the adjustment member 30a in this embodiment of the invention does not become part of the fluid flow channel and is therefore ideal as a simple retrofit of existing nasal cannula apparatus. Usage of this embodiment of the invention by the wearer 5 of the nasal cannula apparatus is nearly identical to that described above with the added advantage of the wearer being able to slide one or more of the adjustment members 30a, 30b, 30c, 30d to the most comfortable positions along the long axis of the first and second fluid supply tubes 20, 15.

Figure 5A:
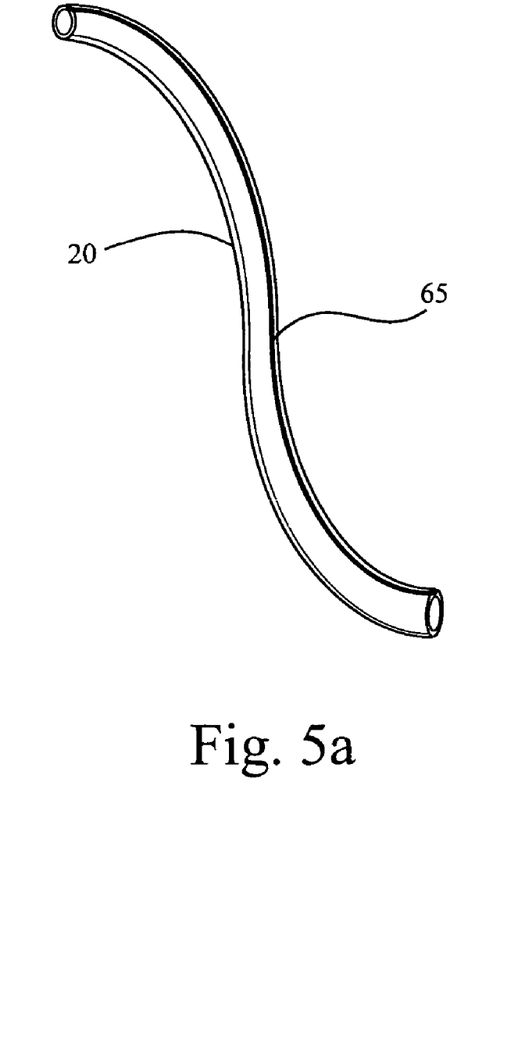
FIGS. 5a-5b depicts an aspect of the invention that incorporates a polymeric fluid supply tube having a non-ferromagnetic ribbon or wire embedded therein as an adjustment member.
Figure 5B:
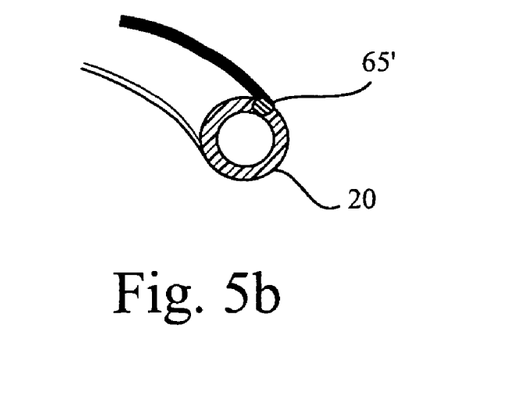

Referring to FIG. 5a, a final embodiment of the invention is shown where a non-ferromagnetic metal ribbon or wire 65 is embedded directly in the first and second fluid supply tubes 20, 15. This embodiment of the invention is simply an extension of the embodiments of the invention described above for FIGS. 4a, 4b, 4c, 4d and 4e where a metal ribbon or wire 65' is incorporated directly into the polymeric construction of the first or second fluid supply tubes 20, 15 as shown in FIG. 5b. This embodiment of the invention provides an additional advantage in that there are no rough surfaces or tubing diameter changes involved in the construction of the nasal cannula apparatus. The wearer 5 of the nasal cannula apparatus which incorporates this embodiment of the invention may simply bend the portion or portions of the first and second fluid supply tubes 20, 15 to the most desirable position without encountering rough edges which could irritate the skin or tubing diameter changes which snag on clothing. All other aspects of this embodiment of the invention are nearly identical to those described above FIGS. 4a, 4b, 4c, 4d and 4e.

The foregoing described embodiments of the invention are provided as illustrations and descriptions. They are not intended to limit the invention to precise form described. In particular, it is contemplated that functional implementation of the invention described herein may be constructed in various shapes and of different materials. No specific limitation is intended to a particular shape or construction material. Other variations and embodiments are possible in light of above teachings, and it is not intended that this Detailed Description limit the scope of invention, but rather by the Claims following herein.

I claim:

1. A nasal cannula apparatus comprising:
    at least one fluid supply tube configured to convey a continuous gaseous flow therethrough, said at least one fluid supply tube having contiguously coupled thereto;
    a nasal insufflating member having a main body in which at least one cross-sectional dimension is greater than a cross-sectional dimension of said at least one fluid supply tube; and,
    at least one adjustment member configured to maintain a contiguous flow path between said at least one fluid supply tube and said nasal insufflating member;
    wherein said at least one adjustment member is only directly in contact with said at least one fluid supply tube;
    wherein said at least one adjustment member alone includes positioning memory means for setting and maintaining a discrete portion of said at least one fluid supply tube in a substantially angular orientation relative to a predominate long dimension of said at least one fluid supply tube, such that said discrete portion of said at least one fluid supply tube is positioned to avoid contact with an ear of a wearer;
    said at least one adjustment member is further configured to direct said discrete portion of said at least one fluid supply tube substantially across a temple area of a wearer at an oblique angle relative to said ear of said wearer; and,
    wherein said at least one adjustment member consists essentially of a malleable non-ferromagnetic metal member embedded longitudinally therein and disposed along said discrete portion of said at least one fluid supply tube.

2. The apparatus according to claim 1 wherein said malleable non-ferromagnetic metal member is one of a wire and ribbon constructed from a metal selected from the group consisting essentially of aluminum, copper and austenitic stainless steel.

3. The apparatus according to claim 1 wherein said substantially non-parallel orientation forms an angle whose apex is approximately in juxtaposition with said ear of said wearer.

4. A method of using the nasal cannula apparatus according to claim 1 comprising:
    positioning said nasal insufflating member in proximity to at least one nostril of said wearer; and,
    manually adjusting said at least one adjustment member such that said at least one fluid supply tube avoids contact with said ear of said wearer.

* * * * *